(12) United States Patent
Kuehnle et al.

(10) Patent No.: US 6,617,153 B2
(45) Date of Patent: Sep. 9, 2003

(54) PORTABLE MAGNETO-MECHANICAL DELIVERY DEVICE AND METHOD FOR DELIVERY OF REACTIVE SUBSTANCES

(76) Inventors: Adelheid Kuehnle, 3119 Beaumont Woods Pl., Honolulu, HI (US) 96822; Manfred R. Kuehnle, 22 Deer Run Rd., Lincoln, MA (US) 01773-2507

( * ) Notice: Subject to any disclaimer, the term of this patent is extended or adjusted under 35 U.S.C. 154(b) by 0 days.

(21) Appl. No.: 10/005,417

(22) Filed: Dec. 5, 2001

(65) Prior Publication Data
US 2002/0127722 A1 Sep. 12, 2002

Related U.S. Application Data

(60) Provisional application No. 60/251,082, filed on Dec. 5, 2000.

(51) Int. Cl.$^7$ .................. C12N 15/87; C12N 13/00; C12M 13/00
(52) U.S. Cl. ............... 435/285.1; 435/283.1; 435/459; 435/285.3; 435/173.5; 435/440; 435/455
(58) Field of Search ............ 435/283.1, 285.1, 435/285.3, 173.5, 440, 455, 459

(56) References Cited

U.S. PATENT DOCUMENTS

| 4,176,172 | A |   | 11/1979 | Bennetch et al. |
| 4,945,050 | A |   | 7/1990 | Sanford et al. |
| 5,036,006 | A |   | 7/1991 | Sanford et al. |
| 5,516,670 | A |   | 5/1996 | Kuehnle et al. |
| 5,759,391 | A | * | 6/1998 | Stadtmuller ............. 210/222 |
| 6,103,127 | A | * | 8/2000 | Pourfarzaneh ........... 210/690 |
| 2001/0028894 | A1 | * | 10/2001 | Gueret ..................... 424/443 |

* cited by examiner

*Primary Examiner*—James Ketter
*Assistant Examiner*—David A. Lambertson
(74) *Attorney, Agent, or Firm*—Saliwanchik, Lloyd & Saliwanchik

(57) ABSTRACT

A method of delivery of reactive substances that are attached to magnetizable needle-like particles using a magneto-mechanical delivery device. The subject method and device can be utilized for the delivery of reactive or other substances, such as DNA via the penetration of a target body. Such penetration of a target or multiple targets can initiate the interaction between the material contained within the target site and the chemical substances delivered by the particles into the targets. In a preferred embodiment, the subject device is portable and does not require electrical power.

26 Claims, 2 Drawing Sheets

PORTABLE MAGNETO-MECHANICAL DELIVERY DEVICE AND METHOD FOR DELIVERY OF REACTIVE SUBSTANCES

CROSS REFERENCE TO A RELATED APPLICATION

This application claims the benefit of U.S. Provisional Application Serial No. 60/251,082, filed Dec. 5, 2000.

FIELD OF INVENTION

The subject invention pertains to the field of genetics, more particularly to the genetic manipulation of cells.

BACKGROUND OF THE INVENTION

When conducting genetic manipulations or other treatments of cells, pollen, organs, or tissue, it is often necessary to partially or completely penetrate the cell walls and/or membranes with a penetrating member to facilitate delivery of biological or other agents. This penetration is necessary to achieve a desired effect on the cell wall and/or internal cellular elements such as the cytoplasm, nucleus, plastids, chromosomes, plasmids, etc. The objective of such a procedure may be, for example, the destruction of selected elements or the production of new or improved biological characteristics. These procedures can be used, for example, to improve by modifying plants, animals, or microbes growth rate, disease resistance, or protein and secondary metabolite production. Other applications include the tagging of cells for tracking and identification, or subsequent micromanipulation over space and time.

Often penetration of cells is accomplished by applying the biological or other agent to carrier particles that are introduced into the cells. Such methods are well known in the art.

In genetic research, for example, such methods are used to penetrate tissue and cells with particles precoated with DNA encoding genes of interest; cell penetration is followed by DNA delivery into the cell nucleus. To reach the intracellular space and then the cell nucleus, the particles must traverse formidable cell walls and membranes. Because these cell walls are difficult to penetrate, the particles carrying the DNA are driven into the cells by the force of an explosive or an electrical discharge. This causes the kinetically driven particles to smash into the target tissue. Even then, to have the necessary energy for penetration, the particles must be several micrometers in diameter. Thus, the implantation process results in appreciable cell damage due to the impact of the particles and/or sonic concussion from the particle-propelling discharge. Some cell tissue, drawing upon its natural strength, may sufficiently recover from this trauma and integrate the newly delivered genetic material into its chromosomes. Other tissue, however, is unable to do so.

These prior methods of delivering particles to cells also lack sufficient control over particle size distribution, particle coating quality, and the velocity and direction of travel of the particles. This results in a lack of predictability and reproducibility of the particle delivery technique. Prior delivery techniques are further disadvantaged because they require the target tissue be maintained in a vacuum, required to penetrate several cell layers deep, which removes moisture from the treated tissue contributing to tissue degradation. In addition, to set up the apparatus for performing the implantations requires time-consuming labor prior to each implantation cycle. Clean up is also time consuming and laborious. As such, the throughputs of the apparatus are relatively low.

Other methods employed or suggested for direct gene delivery to cells include the use of microlasers, microbead vortexing, electrofusion, chemical fusion, microinjection, "whiskers," and electroporation. Such techniques all rely on increasing the permeability of the tissue cells by physically, chemically, or electrically disrupting cell walls and/or membranes temporarily so that exogenously added DNA may then enter the cell through the temporary ruptures. Some of these methods, including microinjection and fusion of pre-selected protoplasts or subprotoplasts, require working at the single cell level. This necessitates micromanipulation of the cells, often involving immobilization by agarose plating or pipette suction. Such micromanipulations must be carried out with a microscope placed in the sterile environment of a laminar flow hood, which can be very cumbersome. As another example, controlled fusion in the production of somatic hybrids, requires bringing the fusion partners into close proximity which is technically difficult to accomplish. Other techniques, such as use of fragile silica-based fibers or "whiskers," involves rapid gyratory or oscillatory motion which obviates directional delivery and re-use of the now fragmented fibers. Such techniques are restricted to use with one or a few types of cells, subcellular targets, or tissues and rarely, if at all, across taxonomic kingdoms, and exclude treatment of tissues in situ.

U.S. Pat. No. 5,516,670 discloses a magnetophoretic method and apparatus for delivering small, needle-shaped, magnetizable particles to a target site. The particles serve as carriers for chemical substances such as DNA, antibodies, or pharmaceuticals which are then presented to the target material in the hope of causing an interaction with said material and bringing a beneficial change to the target host.

The decisive feature described in the aforementioned patent is the ability to move magnetizable particles forward towards the point of convergence of the conical magnetic field, whose gradient along the length of the particle provides the force differential that propels the particle while orienting it vector-like towards the target. In other words, the length of the particle, its magnetizable mass, its magnetic saturation potential, and the magnetic flux density difference between the tip of the acicular particle and its tail where the flux density is less, represent the conditions that collectively result in the force that drives the magnetizable particles into the target site. To obtain the necessary force to overcome the mechanical target resistance such as represented by a cell wall or skin, one endeavors to use powerful magnetic field gradients, long needle-shaped micromagnets of high coercive strength, and sharp tips of the particle to obtain the highest possible penetration pressure at the point where the tips push against said cell walls. These aforementioned conditions determine the mechanical and electrical engineering design of the apparatus, including its electrical energy requirement and, ultimately, its weight and cost.

The main object of the present invention is to reduce the weight and power consumption of such a particle injection apparatus and turn it into a device that is portable to the extent that it can fit into one's pocket and operate without electrical power. To achieve this goal, various attributes and features must be incorporated in a novel device that differs in its very fundamental aspects from what is disclosed in U.S. Pat. No. 5,516,670.

All patents and other publications cited herein are incorporated by reference in their entirety, to the extent not inconsistent with the explicit teachings set forth herein.

BRIEF SUMMARY OF THE INVENTION

The subject invention pertains to a method of magneto-mechanical insertion and retraction of magnetizable particles into a target material by means of a magneto-mechanical delivery device. The device delivers substances such as DNA, chemicals and the like. The subject method and device is utilized for the delivery of substances by effecting the penetration of particles into a target body. Such penetration of a target initiates the interaction between the material contained within the target site and the substance delivered by the penetrating particle. In a preferred embodiment, the subject device is portable and does not require electrical power. The subject magneto-mechanical apparatus can be loaded with reactive substances which are delivered to the target material. Such reactive substances can be carried by needle-like, magnetizable particles, wherein the particles are loaded into one side of the subject device and stand erect and parallel on a loading surface ready to penetrate a target site. The substantially parallel, erect position of the particles is achieved by positioning a magnet such that the field lines of the magnet extend perpendicularly from the substrate, causing the substantially parallel, erect orientation of the particles. The loading surface is moved by mechanical or other means towards a second substrate on which the target material is placed. The two substrates are mated together by a strong non-magnetic force.

Accordingly, it is an object of the present invention to provide a magneto-mechanical delivery service and method for using same.

It is a further object of the present invention to provide a magneto-mechanical delivery device and method for using same that is portable.

It is a still further object of the present invention to provide a portable magneto-mechanical delivery device and method for the delivery of substances to target materials.

It is a still further object of the present invention to provide a portable magneto-mechanical delivery device and method for the genetic manipulation of cells.

Further objects and advantages of the present invention will become apparent by reference to the following detailed disclosure of the invention and appended drawings.

DETAILED DISCLOSURE OF THE INVENTION

The subject invention pertains to a method of magneto-mechanical delivery of particles and a magneto-mechanical delivery device. The subject method and device can be utilized for the delivery of a substance by effecting the penetration of a target body by a particle. Such penetration of a target can initiate the interaction between a material contained within the target site and the substance(s) delivered by the penetrating particle either as payload on the particles or in a medium surrounding the particles.

Figure 1:
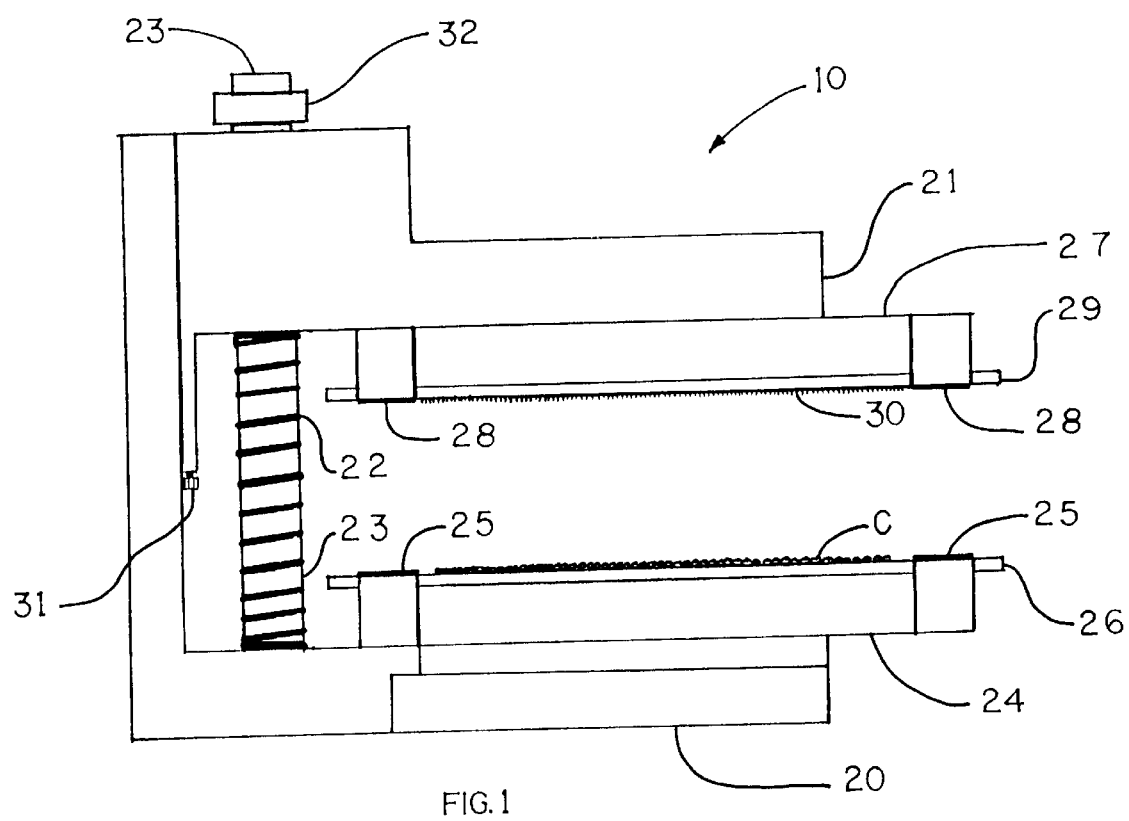
FIG. 1 is a side view of a portable magneto-mechanical delivery device in accordance with the subject invention.

Referring now to FIG. 1, a delivery device in accordance with the subject invention is illustrated and generally referred to as reference numeral 10. The base 20 and moveable arm are substantially parallel and kept separated by spring 22 or other means through which a guide member 23 is complementarily received. The guide member 23 is attached to the base 20 and extends substantially perpendicular through the moveable arm 21.

An optional magnet 24 is removably attached to the base 20 and held in place by holders 25 which may also serve to retain the target substrate 26. Magnet 27 is removably attached to the moveable arm 21 and held in place by holders 28 which also act to hold the loading substrate 29. The loading substrate 29 contains magnetically charged particles 30. Target material C (cells are shown for illustrative purposes) is placed upon the target substrate 26. The particles 30 are treated with the substance to be introduced into the target material, and the moveable arm 21 is pressed against the base 20 so as to bring the particles 30 into contact with the target cells C. A limiting means 31 is attached to the moveable arm 21 to keep the moveable arm 21 from effectively destroying the target material C by the misapplication of pressure.

In a preferred embodiment, the first and second surfaces meet each other as parallel planes. In the embodiment shown in FIG. 1, the loading substrate and the target substrate essentially form closing jaws. A spring 22 is disposed between the upper and lower jaws and maintains separation. A limiting means 31 is located parallel to the spring assembly to regulate the closure distance of the substrates 26 and 29. Alternative embodiments can close via other mechanisms, such as a clamp, piston, or roller, such that the target material C and particles 30 are brought together in an orientation which facilitates penetration of the target material C by the particles 30. Accordingly, these designs allow pressing by mechanical force a plurality of magnetizable particles 30 into a target material C to achieve multiple penetrations therein.

In a preferred embodiment, the subject device is portable and does not require electrical power. In a specific embodiment, the subject magneto-mechanical apparatus is loaded with reactive or other substances which are to be delivered to a target site. For example, such substances can be carried by acicular, magnetizable particles, wherein the particles are loaded onto one side of the subject device so as to stand substantially parallel and erect on the loading surface ready to penetrate the target site. In another example, the reactive or other substances can be carried in a semi-solid or liquid medium, or in an ice sheet surrounding the particles loaded on the subject device. In a further example, the substances of interest can be incorporated in a medium that bathes the target tissue and enters the tissue as particles penetrate the medium and the target tissue.

A substantially parallel, erect position can be achieved for the particles by locating a magnet near or at the loading substrate. The magnet is positioned with respect to the loading surface such that the field lines of the magnet extend perpendicularly from such surface, causing the substantially parallel, erect orientation of the particles. Parallel alignment is more effective when the loading surface is at a distance from 0.5 cm to several centimeters from the magnet. The loading surface is moved by mechanical or other means towards a second surface on which a target material is placed. The two surfaces are moved towards each other by a non-magnetic force. In order to keep the particles erect in the space between the loading surface, a first magnet is located behind the loading surface. A second magnet can be located behind the target surface so that the two magnets together make a stronger magnetic field to help keep the magnetizable particles erect and substantially perpendicular (or otherwise oriented as desired) to the surfaces.

The target substrate, the loading substrate, or both can incorporate removable magnets to correct and maintain the position of the magnetizable particles 30. The subject particles 30, treated or untreated with reactive or other substances, stand erect and substantially parallel to each other on the loading surface, and preferably should remain in that manner as the substrates are brought together. Alternative orientations of the particles may be desired and can also be achieved. For example, it may be desirable to have the particles at an angle to the surface (if the surface holding the target material is unrolled onto the surface associated with the particles. In another embodiment, a permanent magnet is associated with each substrate. Electromagnets can also be utilized.

Particles are loaded shortly before use in a dry or liquid state, with or without a substance payload. Particles can also be loaded en masse using a pre-prepared particle packet (not shown). A particle packet loaded onto one substrate can consist of a foil through which the particles are mounted during a preparatory production step. The resulting assembly resembles a dense needle brush with a tape-like backing. A particle packet can also be composed of particles embedded in a semi-solid gel or ice supported by a flat glass or plastic backing. The glass or plastic support can become the loading surface after being inverted and stuck onto the magnet (e.g., by utilizing doublesided tape or other attachment means as would be readily apparent to the skilled artisan). To prepare the packet, particles are loaded in molten gel or liquid medium onto the backing positioned well above the region of a flat bar magnet corresponding to the desired orientation of magnetic field lines, lowered directly onto the magnet to align the particles, then cooled to allow gel solidification or ice formation.

The target material can include an aggregation of cells, embryos, pollen, or even larger structures such as leaves. Target material can also comprise cells or tissues in situ, such as plant reproductive structures, animal and human skin for DNA vaccines, animal and human deep tissue, and animal and human tumors. Magneto-mechanical treatments are performed in such a manner that the treated cells do not separate from the host organism. This allows the cells to continue to function normally with modification.

The target material can also be mounted on an adhesive tape-like backing. A backing support such as flat glass or plasticware can also be used for loading the target material either directly or with an interface of water or other medium between the backing material and the target.

If a tape-like backing is used for both the particles and target material, the adhesive surfaces preferably face each other such that, when pressed together, the tapes adhere at their perimeter, so as to essentially maintain the relative positions of the particles and the target materials. This results in a "sandwich" configuration made up of the particles, target material, and tape backing can then be removed from the jaws as a single entity. It is peeled apart at a later time (e.g., after a gestation period). The non-adhesive surfaces of the backing tapes can be used to record sample description, dates, codes, and the like. Color coding the backing tapes can also be implemented. A retaining member 32 on guide member 23 can be utilized to keep the surfaces together and otherwise seal the device, especially when a single magnet is used, until separation is desired.

If no tape-like backing is used for sealing the device, the optional magnet can be utilized and the particle/target sandwich remains closed due to magnetic attraction of the top and bottom magnets to each other. The mated surfaces remain together until mechanically separated.

The subject particles can be coated with reactive or other substances which are to be delivered into the cell targets, for example to react therein. Such substances can also be dispersed in a material surrounding the magnetizable particles such as a semi-solid gel, ice, or liquid medium. A densely packed particle assembly can be utilized such that a high percentage of penetrations and substance deliveries can be achieved.

Magnets 24 and 27 located near the substrates 26 and 29 assure that particles 30 are oriented in the proper direction such that they penetrate tip first into the densely packed target material C. Preferably, the clamp utilizes a mechanical limiting means 31 which permits setting a minimum gap between the substrates 26 and 29. This gap can help to minimize breaking or bending of the needles and squashing the target material. The parallel magnets above and below the target can be slipped in and out of holders 25 and 28. This allows for their substitution to alter strength and dimension. The parallel magnets 24 and 27 can also be magnetically stacked one magnet on top of the next to alter the gap distance between them. In an alternative embodiment, the magnet 27, with the loading substrate 29 and magnetizable particles 30, can be can be attached to the base 20 rather than the moveable arm 21. In addition, the target material C can be loaded with the magnetizable particles 30 on the same substrate separately or in a particle packet or matrix.

Figure 2:
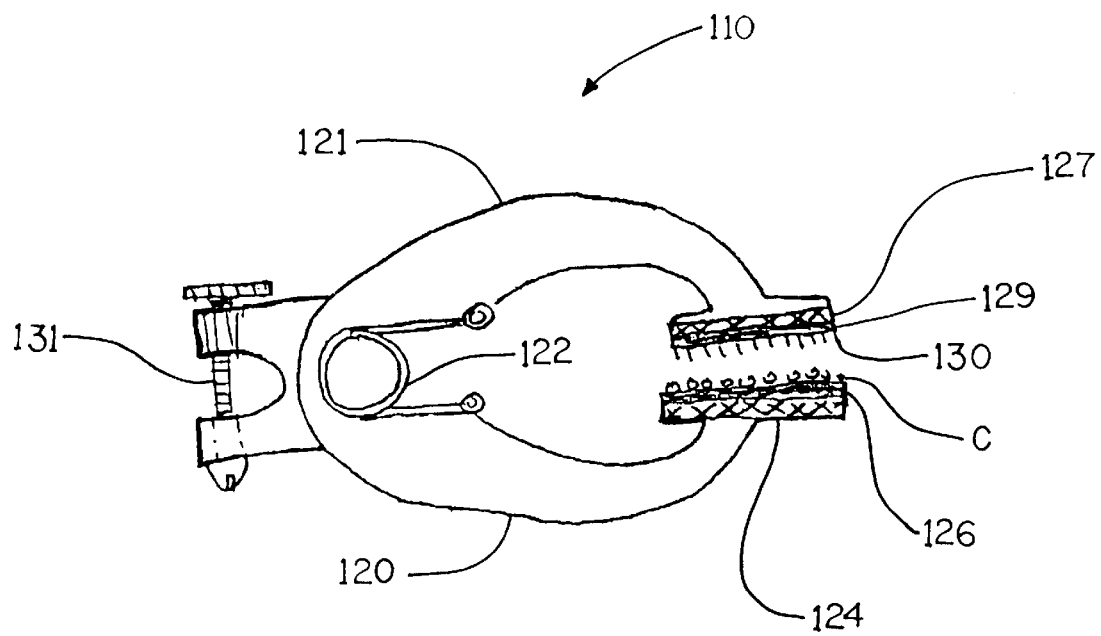
FIG. 2 is a side view of an alternative embodiment of a magneto-mechanical delivery device in accordance with the subject invention.

Referring now to FIG. 2, an embodiment which appears like a clamp with two jaws is shown and generally referred to as reference number 110. This device can be opened and closed, for example, by cam action or handles similar to pliers. The lower arm 120 and upper arm 121 are substantially parallel. The lower arm 120 and upper arm 121 are separated by a spring 122 or other means. Attached to one end of lower arm 121 is an optional magnet 124 which is removable. The target substrate 126 is removably attached to the end of the lower arm 120 and can serve to hold the target material C. The upper arm 121 has a removable magnet 127 at one end. The loading substrate 129 is removably attached to the end of the upper arm 121 and between the removable magnet 127 and magnetizable particles 130. The device can be easily inverted such that arms 120 and 121 become the upper and lower arms respectively.

A limiting means 131 acts to limit the pressure applied to the target material. It allows the magnetizable particles 130 to penetrate the target material C without destroying the target material C by the misapplication of pressure. It is important to provide the necessary force for pressing together the jaws to achieve penetration of the subject particles into the target material.

Figure 3:
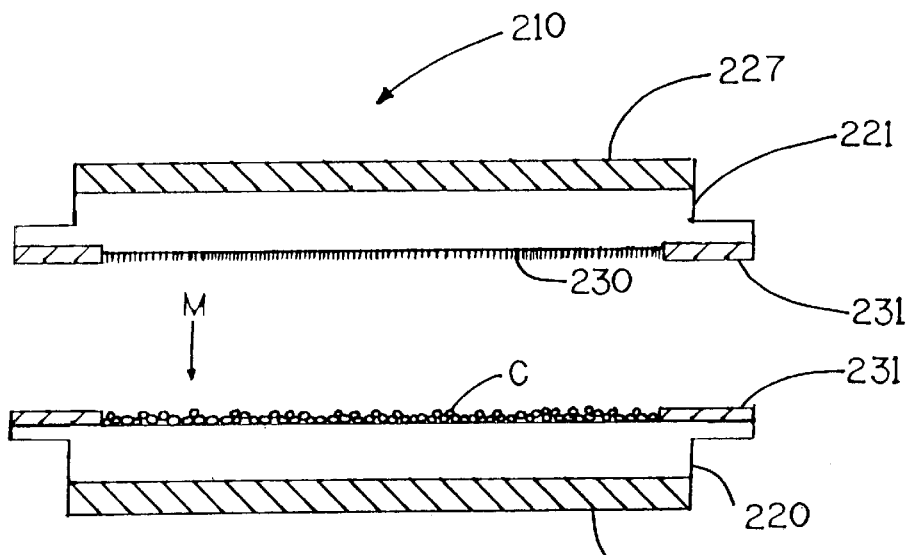
FIG. 3 is a frontal view of an embodiment magneto-mechanical delivery device in accordance with the subject invention.

Referring now to FIG. 3, an alternate configuration is shown in accordance with the subject invention and generally referred to as reference number 210. The base 220 and mating surface 221 are substantially parallel and act as the substrates for the particles 230 and target material C. An optional magnet 224 is removably attached to the base 220 to strengthen the magnetic field M. Magnet 227 is removably attached to the mating surface 221 and acts to correctly position the particles 230. The base 220 and mating surface 221 are pressed together thereby bringing the particles 230 into contact with the target cells. Spacers 231 act as a limiting means to allow the particles 230 to adequately penetrate the target material C and yet keep the mating surface 221 from effectively destroying the target material C by the misapplication of pressure.

Following are examples which illustrate procedures for practicing the invention. These examples should not be construed as limiting. All percentages are by weight or numbers, and all solvent mixture proportions are by volume, unless otherwise noted.

EXAMPLE 1

In one embodiment, approximately 2000 nickel-cobalt magnetizable particles (micromagnets) of 500 micron length, 4 micron width with serpentine edges, are coated using a standard precipitation mix of 20 µl 0.1 M spermidine/50 µl 2.5 M calcium chloride with DNA of pAGM148 (20 microgram per 130 µl coating mix) in 12% polyethylene glycol (MW~3500), modified such that no final ethanol rinse is made. Micromagnets, in volumes of 65, 130 and 500 µl, are spread over a desired area by a pipette tip, and are mounted vertically and in parallel on a first sterile plastic surface 1 cm above a 2" square neodymium magnet. Leaf explants of tobacco and Petunia hybrida, harvested from aseptically grown plants on Murashige and Skoog medium as known in the art, are positioned non-randomly abaxial side down directly on top of the stationary liquid containing the oriented magnetized particles. This is opposed in parallel and above by a rectangular 1"×2" ceramic magnet on a second sterile plastic surface to form a sandwich around the leaf when mated. Crushing is prevented by a limiting means such that larger protruding veins are slightly compressed but not the overall blade. Micromagnets are maintained rigid and oriented in the vertical and do not break during the innoculation time. Innoculation occurs after approximately a 10 minute compression of the sandwich. This is observed subsequently at 40× on a Nikon dissecting microscope. The magnets are pulled apart and the magnetized particles are extracted and removed from the tissue by an external magnet, such as a quarter-inch cylindrical permanent magnet, passed over the leaf surface; these particles are saved for reuse. Leaf tissues, cultured for 36 hours after treatment on top of hormone-free Murashige and Skoog medium solidified with 0.8% agar, are placed in GUS (for beta-glucuronidase reporter gene activity) staining solution with 20% methanol. Blue GUS positive trichomes and mesophyll cells are observed after overnight staining in magneto-mechanically treated tissues but not in untreated (no DNA) control tissues.

Transgenic plants are recovered from similarly treated leaves that are grown in light for 2–3 months on shoot regeneration medium containing 300 mg/L kanamycin or other selectable marker compound appropriate for the transforming plasmid. These plants are not placed in GUS staining solution. Shooting medium is a Murashige-Skoog basal medium with 3% sucrose, Gamborg's B5 vitamins, and 2.7 g/L Phytagel or 0.7% agar, with 2 mg/L 6-benzylamino-purine for tobacco or 3 mg/L 6-benzylamino-purine plus 0.1 mg/L IAA for petunia. Different studies confirm similar observations using different numbers of micromagnets and varying treatment conditions including magnetizable particles both on top and on bottom of a leaf.

EXAMPLE 2

In another embodiment, magnetizable particles are delivered to a precise location for transgene expression in complex tissues. Specifically, DNA-coated magnetizable particles as in the above leaf example are manually positioned in drops above the meristems of multiple longitudinally dissected cotton embryos that were previously disinfested, imbibed, and stripped of outer seed coats and most cotyledon tissue. Dissected tissue is mounted cut surface-up on the first sterile plastic surface about 1 cm above a 2" neodymium magnet; the magnetizable particles vertically align when near the tissue. Multiple particles are substantially parallely embedded into the cotton tissue by a second sterile surface as seen by observation on a dissecting microscope. Specifically, the particles are embedded into the meristem regions. Particle penetration can occur without a second parallel magnet. Magnetizable particles are then extracted by an external magnet. GUS staining shows positive blue cell foci in magneto-mechanically treated tissues but not in untreated (no DNA) control tissues.

EXAMPLE 3

In another embodiment, tobacco is engineered at the plastid level by using any of the plastid transformation vectors known in the art. (See Bock and Hagemann, *Prog. Bot.* 61:76–90 (2000) and Guda et al., *Plant Cell Reports,* 19:257–262 (2000) and references therein). *Nicotiana tabacum var. 'Xanthi NC' leaf sections* (1×0.5 cm strips from in vitro plants with 3 to 5 cm long leaves) are centered in the dish, top side down on pre-aligned magnetizable 500 micron particles coated with DNA in polyethylene glycol (PEG)or in polyethylenimine (PEI) [from Polyplus transfection, Cedex, France], using a magneto-mechanical device, as described above for leaf tissue. After treatment, the tissues are cultured under lights on callus or shoot regeneration medium (RMOP shoot regeneration medium or on a Murashige-Skoog salts shoot regeneration medium with 3% sucrose, Gamborg's B5 vitamins, 2 mg/L 6-benzylamino-purine, and 2.7 g/L Phytagel) containing 500 mg/L spectinomycin or streptomycin, or 50 mg/L kanamycin increased to 500 mg/L during the following 3 to 8 weeks, plated onto fresh medium every 3 weeks. De novo green growth, forming shoots, is visible soon after. It is removed and undergoes a second round of selection on shoot regeneration medium with antibiotics. This encourages homoplasmy. Genomic DNA is isolated from leaf tissue derived from in vitro germinated transplastomic seeds utilizing the DNeasy Plant Mini Kit (Qiagen Inc, Valencia, Calif.) according to the manufacturer's instructions. Further, it is subjected to PCR and/or Southern analysis to confirm plastome integration and homoplasmy by detection of products of predicted sizes following published protocols using primers specific for plastid vector flanking sequences as known in the art.

EXAMPLE 4

In another embodiment, microalgae-chloroplast transformants are obtained by magneto-mechanical treatment of *Chlamydomonas reinhardtii* cells. This is followed by subsequent selection on spectinomycin using a plasmid vector with the coding sequence of the aadA gene, (e.g., pUC18 derived vector containing 5-atpA:aadA:rbcL-3) as known in the art. About 10,000 microalgae cells are spread over a Nytran nylon 0.45 micron membrane, surface dried briefly, then inverted over pre-aligned DNA-coated magnetizable particles as described above. The particles are embedded into the cells following a magnetic sandwich treatment with the membrane lowered onto the particles by a second sterile surface onto which the moist membrane is attached by surface tension and above which is a second bar magnet. After treatment, the nylon membrane is placed on top of TAP plates containing 200 to 800 mg/L spectinomycin. Plates are incubated in low light for two to three weeks before colonies are counted. Antibiotic-resistant colonies are green (vs yellowish for susceptible cells) and transformants are characterized using skills as known in the art.

EXAMPLE 5

In another embodiment, the magneto-mechanical injector device is used to induce malaria-specific antibody and T cell responses, using the *Plasmodium falciparum* MSP1-42 DNA vaccine and recombinant MSP1-42 protein as immunogens. Magnetizable particles of 500 micron length with serpentine edges, and 800 micron length with hollow tails for deeper tissue, are used. Outbred Swiss Webster mice (10 per study group) are immunized with micromagnets coated with MSP1-42 plasmid (or recombinant protein) in varying doses. Particles are delivered trans- and sub-cutaneous to the shaved right and left thighs. A total of 3 immunizations at 28 day intervals are given. Immunization treatments are micromagnets (0.01% w/v, 100 μL per treatment) coated in spermidine/calcium chloride in 12% PEG with 50, 200 μg of plasmid, or 5, 10 μg of recombinant MSP1-42. The micromagnets are inserted into the hand-held magneto-mechanical device using packets of pre-aligned, immobilized magnetizable particles (frozen in DNA-coating solution or in a thin layer of 0.5% sodium alginate solidified with an aerosol spray of 2% calcium chloride). The packets are aligned perpendicular to the mouse thighs for antibody studies and to the base of tails for T cells studies. The particles are applied for 25-second penetration periods using a dual neodymium magnet system. Double packets (top and bottom of target tissue) can also be utilized.

Mice are bled prior to immunizations and in intervals after each immunization for measurements of total antibody titers by ELISA as is known in the art. Briefly, ELISA plates are coated with the recombinant MSP1-42 antigen at 1.0 μg/ml and blocked with 1% BSA. Sera are diluted 100 fold in 1% BSA and incubated in antigen-coated wells for 2 hours. Plates are washed and incubated with HRP-conjugated, goat-anti-mouse, rabbit or monkey immunoglobulin (Ig) (or IgG+IgM) as the secondary antibody (KPL Inc., Zymed Inc.) for 1 hr. Washed wells are then incubated in peroxidase substrate (H2O2+ABTS (KPI, Inc)). Optical densities are measured at 410 nm with a BioRad ELISA reader. Significant levels (Student's t-test) of anti-MSP1 antibodies are detected in mice immunized with the magneto-mechanical device as compared to non-immunized mice.

To illustrate the induction of T cell responses to MSP1-42 antigens by magneto-mechanical delivery, Balb/c and C57B1/6 mice (10 per study group) are used. Mice are immunized with the MSP1-42 plasmid (or recombinant protein)—coated micromagnets in varying doses. Particles are delivered to the base of the tail. A total of 3 immunizations at 14 days intervals are given. Conventional in vitro antigen-driven T cell proliferation assays are then used. Briefly, seven days after the last immunization, spleen cells as well as lymph node cells are harvested and T cells are purified as known in the art. Cultures are incubated in flat-bottom microtiter plates at a concentration of $4 \times 10^5$ cells per 200 μl RPMI 1640 culture medium for 3 days in a humidified atmosphere of 5% $CO^2$. At 24, 48 and 72 hrs, culture supernatants are removed and assayed for cytokines production (IL-2, IL-4, IL-5 and IFN-γ) by commercially available ELISAs (R&D Sys., and Pharmingen). Significant levels of in vitro antigen-driven, MSP1-specific T cell responses in mice immunized with the mechanomagnetic magnetophoresis injector as compared to non-immunized mice are detected. Monitoring of injection sites for inflammation and of husbandry behaviors of the immunized animals shows no adverse effects of the immunization procedures.

In as much as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

We claim:

1. A magneto-mechanical device for the delivery of substances into a target material comprising:
    a) a first surface comprising a plurality of magnetizable particles wherein said magnetizable particles protrude substantially perpendicular from the face of said first surface;
    b) a second surface substantially parallel to the first surface;
    c) at least one magnet for positioning said magnetizable particles; and
    d) a means to bring said first surface and said second surface towards each other whereby magnetizable particles contact a target material which has been placed on either said first surface or said second surface so as to cause said particles to penetrate the target material, thereby delivering a substance on said particles into the target material.

2. The magneto-mechanical delivery device of claim 1 wherein said device is portable.

3. The magneto-mechanical delivery device of claim 1 wherein said magnetizable particles have at least one sharp end.

4. The magneto-mechanical delivery device of claim 1 wherein said magnetizable particles are recoverable from the target material.

5. The magneto-mechanical delivery device of claim 1 wherein said magnetizable particles are contained in a particle packet.

6. The magneto-mechanical delivery device of claim 5 wherein said particle packet also contains target material.

7. The magneto-mechanical delivery device of claim 1 wherein said magnetizable particles are contained in a matrix.

8. The magneto-mechanical delivery device of claim 7 wherein said matrix also contains target material.

9. The magneto-mechanical delivery device of claim 7 wherein said matrix has an adhesive backing.

10. The magneto-mechanical delivery device of claim 7 wherein said matrix comprises magnetizable particles mounted in a foil carrier.

11. The magneto-mechanical delivery device of claim 7 wherein said matrix is liquid.

12. The magneto-mechanical delivery device of claim 7 wherein said matrix is a gel.

13. The magneto-mechanical delivery device of claim 7 wherein said matrix is frozen.

14. The magneto-mechanical delivery device of claim 1 wherein said means to bring said first and second surfaces towards each other comprises a base and a moveable arm substantially parallel to said base.

15. The magneto-mechanical delivery device of claim 14 wherein said moveable arm is retractable.

16. The magneto-mechanical delivery device of claim 14 wherein said moveable arm is manually operated.

17. The magneto-mechanical delivery device of claim 14 wherein said moveable arm is operated by a clamp, a piston, or a roller.

18. The magneto-mechanical delivery device of claim 14 wherein said moveable arm has a limiting means.

19. The magneto-mechanical delivery device of claim 18 wherein said limiting means is adjustable.

20. A particle pack for the magneto-mechanical transfer of substances to a target material comprising needle-like magnetizable particles contained in a matrix wherein said magnetizable particles are substantially parallel to each other.

21. The particle pack of claim 20, wherein said matrix also contains target material.

22. The particle pack of claim 20, wherein said matrix comprises an adhesive backing.

23. The particle pack of claim 20 wherein said matrix comprises magnetizable particles mounted in a foil carrier.

24. The particle packet of claim 20 wherein said matrix is a liquid.

25. The particle packet of claim 20 wherein said matrix is a gel.

26. The particle packet of claim 20 wherein said matrix is frozen.

* * * * *